United States Patent [19]

Miyatake et al.

[11] Patent Number: 4,499,378
[45] Date of Patent: Feb. 12, 1985

[54] INFRARED RADIATION GAS ANALYZER

[75] Inventors: Kimio Miyatake; Kozo Ishida; Hiroyuki Ebi; Takeshi Shimada, all of Kyoto, Japan

[73] Assignee: Horiba, Ltd., Kyoto, Japan

[21] Appl. No.: 473,344

[22] Filed: Mar. 8, 1983

[30] Foreign Application Priority Data

Mar. 9, 1982 [JP] Japan .............................. 57-33704[U]
Mar. 9, 1982 [JP] Japan .............................. 57-33705[U]

[51] Int. Cl.³ ................................................ G01J 1/00
[52] U.S. Cl. ...................................... 250/343; 250/352
[58] Field of Search .................... 250/338 R, 343, 344, 250/352; 356/437

[56] References Cited

U.S. PATENT DOCUMENTS 3,794,838  2/1974  Weiss et al. .......................... 250/352
3,968,370  7/1976  Luft ...................................... 250/343
4,233,513  11/1980  Elder et al. .......................... 250/352
4,373,137  2/1983  Fabinski et al. ...................... 250/343

FOREIGN PATENT DOCUMENTS 58-17343  2/1983  Japan ................................... 356/437

Primary Examiner—Janice A. Howell
Attorney, Agent, or Firm—Wenderoth, Lind & Ponack

[57] ABSTRACT

An infrared radiation gas analyzer for determining the concentration of an ingredient in a sample gas has a sample gas container for containing a sample gas at a temperature at which the ingredient the concentration of which is to be determined will emit infrared radiation in a range characteristic of the ingredient and a window for allowing the infrared radiation to escape from the container. An optical chopper is positioned outside the container for interrupting the radiation escaping from the container. A filter is positioned in the path of the radiation escaping from the container and transmits only radiation in the range. An infrared radiation detector is positioned for receiving the radiation passed by the filter and emitting a signal representative of the radiation received by the detector and which is representative of the concentration of the ingredient the concentration of which is to be determined in the sample gas.

8 Claims, 8 Drawing Figures

INFRARED RADIATION GAS ANALYZER

BACKGROUND OF THE INVENTION

1. Field of the Invention

This invention relates to an infrared radiation gas analyzer for determining the concentration of a specified ingredient in a sample gas, which analyzer is simple and has an inexpensive construction from which an infrared light source and a power source for stabilizing the light source, previously required in a conventional infrared gas analyzer, have been eliminated. The analyzer heats a sample gas and measures the infrared radiation having characteristic wave lengths of the ingredient and radiated from the ingredient in the heated sample gas.

2. Description of the Prior Art

A nondispersive infrared absorption method has often been used for the determination of the concentration of an ingredient in a gas. This method utilizes Lambert-Beer's law, that is to say, the fact that the strength of infrared rays transmitted through the gas is reduced as a function of the concentration of the ingredient in the gas and the cell length as shown by the following equation (1):

$$I = I_0 \exp(-kCl) \tag{1}$$

in which

I: the strength of infrared rays after transmitting through gas;
$I_o$: the strength of incident rays;
k: constant;
c: concentration of the ingredient in the gas; and
l: cell length FIG. 1 shows one embodiment of a conventional infrared gas analyzer utilizing the nondispersive infrared absorption method. Referring now to FIG. 1, an infrared light source 1' having tungsten lamps or the like, has a light quantity balancer 2', and the lamps are directed through a sample cell 3' and a reference cell 4'. A chopper 5' is provided at the output ends of cells 3' and 4' and chops the emitted radiation falling on an infrared detector 6' such as a condenser microphone. In the nondispersive infrared absorption method carried out in this apparatus, the incident ray is from said infrared light source 1'. Any change in the quantity of light from said infrared light source 1' leads to errors of measurement, and consequently a power source for the light source must maintain the quantity of light from said light source 1' constant. The construction of the power circuit for such a power source becomes complicated and expensive. Moreover, when carrying out the nondispersive infrared absorption method, when using the reference cell 4', optical adjustment of the quantity of light incident upon both of said cells 3' and 4' is necessary for preventing drift owing to the deterioration of said light source 1' and fouling of said cell 3'.

SUMMARY OF THE INVENTION

The present invention provides an infrared radiation gas analyzer for determining the concentration of an ingredient in a gas which overcomes the problems of the prior art apparatus. In the analyzer of the invention, concentration is determined from the infrared radiation from the ingredient and detected by an infrared detector. The analyzer comprises a sample cell for containing the sample gas, a heater for heating the sample gas, an optical chopper in the path of the radiation from the gas in the cell, a filter for transmitting from among the infrared rays radiated from the sample gas heated by said heater only infrared rays characteristic of those radiated from the ingredient the concentration of which is to be determined, and an infrared detector for detecting infrared rays transmitted through said filter.

According to the present invention, infrared rays above the certain level are radiated from a sample gas when the sample gas is heated, and the comparatively small infrared radiation from the ambient air of the cell, the optical chopper and the like, is negligible. Consequently, the infrared radiation from the ingredient contained in the sample gas and the concentration of which is to be determined can be measured, and this measurement is used for the determination of the concentration of the ingredient. Thus an infrared gas analyzer which has a simple construction and is inexpensive can be provided because it has no infrared light source and no power source for stabilizing the light source such as have been required in the conventional infrared gas analyzer.

This is possible because gas molecules, other than monoatomic molecules, radiate characteristic infrared rays having certain wave lengths when they are heated to high temperatures. The radiant coefficient of these infrared rays is dependent upon temperature and the quantity (partial pressure of the molecules) x (cell-length), as shown in for example FIG. 2 and FIG. 3. It can be shown to be a function of the partial pressure of the molecules, i.e. concentration of the molecules in the sample gas, at constant temperature, cell-length and partial pressure.

The infrared radiation gas analyzer of the present invention utilizes this principle.

The above described principle can be explained as follows, using as an example the concentration of $CO_2$ in a sample gas.

First, the sample gas is heated to a temperature that the infrared radiation from the $CO_2$ gas in the sample gas exceeds the detecting sensitivity of the detector to be used. In this case, it is to be desired that only radiation in the 4.3 $\mu$m band, which is generated owing to the vibration-rotational transition between (00°0)–(00°1) and which is the strongest of several infrared band spectrums of $CO_2$ molecules, be measured. A band pass filter having a central wave length of 4.3 $\mu$m is placed between the sample gas and the infrared detector in order to achieve this object. Thus only infrared rays in a band around 4.3 $\mu$m from among all the infrared rays radiated from the sample gas heated to high temperatures are allowed to impinge on the infrared detector. An electric signal which is proportional to the radiation strength $N_T$ as expressed by the following equation (2), is generated by the infrared detector:

$$N_T = \int_{\lambda_1}^{\lambda_2} T\lambda \tau \lambda (\alpha\lambda \cdot T + \beta\lambda T) e\lambda \cdot T^{\alpha\lambda} \tag{2}$$

wherein $N_T$: the radiation strength of the 4.3 $\mu$m band at the temperature T; $\alpha\lambda$: the spectral sensitivity of the infrared detector; $\tau\lambda$: the spectral transmissivity of the 4.3 $\mu$m band pass filter; $\alpha\lambda.T$: the radiation coefficient of $CO_2$ gas at the temperature T; $\beta\lambda T$: the radiation coefficient of the windows and wall surfaces; $e\lambda.T$: the spectral radiation brightness of a black body; $(\lambda_1, \lambda_2)$:

the transmission wave length range of the band pass filter; and λ: the wave length (μm).

In the equation (2), the spectral sensitivity of the infrared detector αλ, the spectral transmissivity of the band pass filter τλ and the radiation coefficient of the windows and wall surfaces βλT are those for the analyzer, and the spectral radiation brightness eλ.T of a black body is calculated by Planck's equation. Therefore the spectral radiation coefficient αλ.T of the 4.3 μm band of $CO_2$ can be calculated from $N_T$. αλT is dependent upon the temperature, pressure, wave length, cell-length and concentration (partial pressure of $CO_2$) and accordingly, the partial pressure of $CO_2$ (concentration) can be determined by measuring the infrared radiation in the band around 4.3 μm under constant temperature, cell-length and pressure conditions.

Consequently, the concentration of $CO_2$ contained in a sample gas can be determined from the thus measured infrared radiation.

BRIEF DESCRIPTION OF THE DRAWINGS

The invention will now be described in greater detail in connection with the accompanying drawings in which.

DESCRIPTION OF THE PREFERRED EMBODIMENTS

Figure 1:
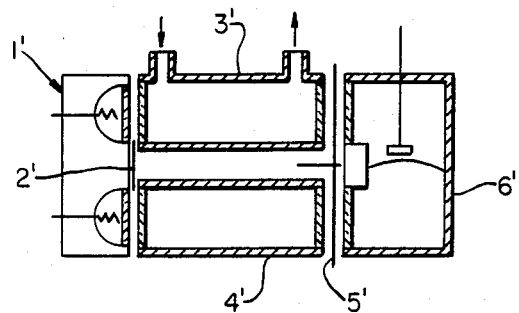
FIG. 1 is a schematic sectional view of a conventional infrared gas analyzer.
Figure 2:
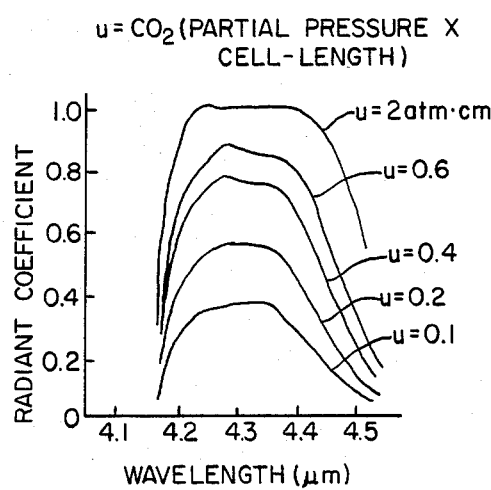
FIG. 2 is a graph showing the relation between the infrared radiation coefficient and wave length of radiation from a sample gas for various values of cell-length x concentration of $CO_2$ and for constant temperature and pressure conditions.
Figure 3:
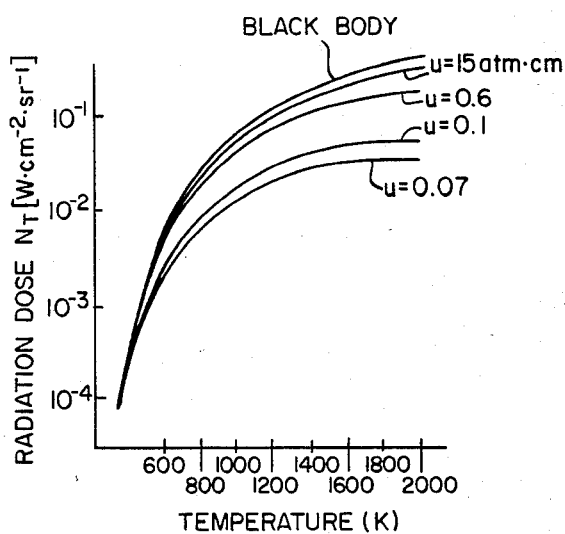
FIG. 3 is a graph showing the relation between temperature and radiation.
Figure 4:
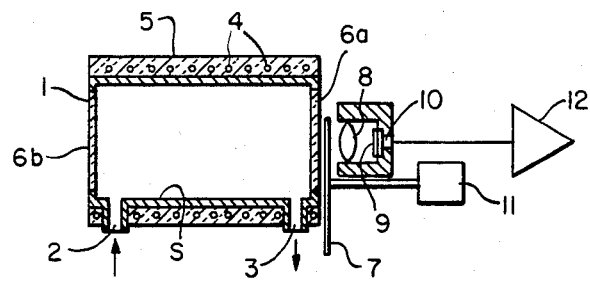
FIG. 4 is a schematic sectional view of one embodiment of an infrared radiation gas analyzer according to the present invention.

As shown in FIG. 4, the analyzer of the invention comprises a sample cell 1 provided with an inlet 2 for a sample gas and an outlet 3 for the sample gas, and which has a resistance heater 4 wound around the cell for heating a sample gas which is put into said sample cell 1 to a high temperature, e.g. higher than 100° C., said heater 4 being covered with insulating material 5. Windows 6a and 6b for transmitting infrared rays are provided at the opposite ends of cell 1, and an optical chopper 7 is placed outside one window, the window 6a in this embodiment, and is driven by motor 11. A condensing lens 8 is provided on the opposite side of the chopper from the window 6a, and a band pass filter 9 is positioned behind the condensing lens and transmits infrared rays in the specified wave length from the ingredient the concentration of which is to be determined to an infrared detector 10 which receiving the infrared rays transmitted through said band pass filter 9. Pneumatic type detectors, in which the ingredient the concentration of which is to be determined or gas having the same range of absorption wave lengths as the ingredient the concentration of which is to be determined is enclosed, can be used for said infrared detector 10 as well as heat detectors such as pyroelectric detectors and thermopile detectors and solid detectors such as semiconductor detectors. An amplifier 12 receives electric signals from said infrared detector 10 and amplifies them and supplies them to a concentration indicator, not shown.

In the above described analyzer, infrared rays are radiated from the sample gas when the sample gas at a constant pressure in said sample cell 1 is heated to the appointed temperature by means of said heater 4. The infrared rays of the specified wave length, for example in the 4.3 μm band for the determination of concentration of $CO_2$, radiated from the ingredient the concentration of which is to be determined are received by said infrared detector 10 through said lens 8 and band pass filter 9. The concentration of the ingredient in the sample gas is represented by the signal from said infrared detector 10, which signal corresponds to the infrared radiation due to the presence and concentration of ingredient in the sample gas.

In the above described embodiment, the internal surface of said sample cell 1 is preferably mirror surface S in order to minimize an infrared radiation from the internal surface of said sample cell 1, and the end opposite that which said infrared detector 10 is located has the window 6b therein which is made of the same material as said window 6a and transmits infrared rays in the same manner as the window 6a. However, this is not an indispensable feature of the present embodiment. Furthermore, said heater 4 is set so as to heat the sample gas to the appointed temperature. The heater 4 can be adjustable and be set so as to heat a sample gas to any suitable temperature range, and a thermometer can be provided for measuring the temperatures of a sample gas and be connected to control means for the heater to carry out temperature adjustment in case the temperature of the sample gas varies from the desired temperature.

Figure 5:
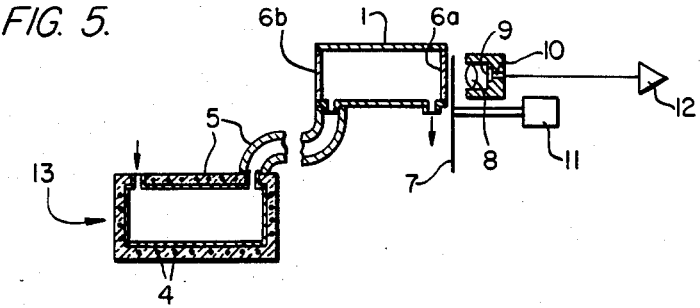
FIGS. 5, 6, 7 and 8 are respectively schematic sectional views similar to FIG. 1 of other embodiments of the infrared radiation gas analyzer according to the present invention.

FIG. 5 shows another embodiment of the present invention. This embodiment differs from that of FIG. 4 in that a separate heater 13 is provided which has a heater 4 surrounding the outside surface of a sample gas flow path means upstream of said sample cell 1, and sample gas which has been previously heated is introduced into said sample cell 1.

With this arrangement, the shape and material of the cell can be freely selected and said infrared detector 10 can easily be kept cool since said heater 4 is at a distance from said infrared detector 10. Furthermore, the influence of infrared rays radiated from said sample cell 1 can be eliminated since the temperature of said sample cell 1 itself can be kept low.

Figure 6:
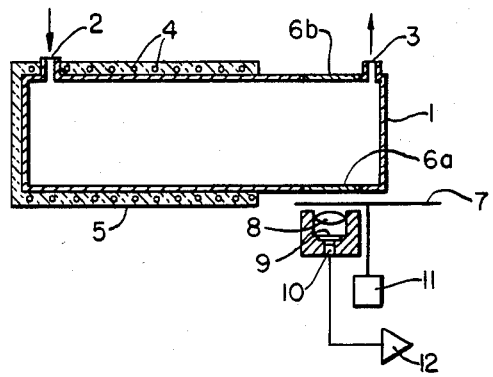

FIG. 6 shows still another embodiment of the present invention. In this embodiment, said sample cell 1 has the heater 4 surrounding only a part thereof near said inlet 2 for the sample gas, and said windows 6a and 6b for transmitting infrared rays are on opposite sides of the cell in a direction across the path of the gas inside said sample cell 1 and near said outlet 3. The infrared detector 10 is placed opposite one of said windows, in this case the window 6a. In this embodiment, the influence of infrared rays radiated from the cell itself can be reduced. In addition, there is no long passage between the heating region and the region from which the rays are passed through the window 6a since said heater 13 is integral with said sample cell 1, and moreover the temperature of the sample gas can be prevented from falling after it has once been heated.

It is also possible to make said sample cell 1 as shown in FIG. 6 entirely of infrared ray-transmitting material.

Other than the parts of the embodiments of FIG. 5 and FIG. 6 described above, the embodiments are the same as that shown in FIG. 4.

Figure 7:
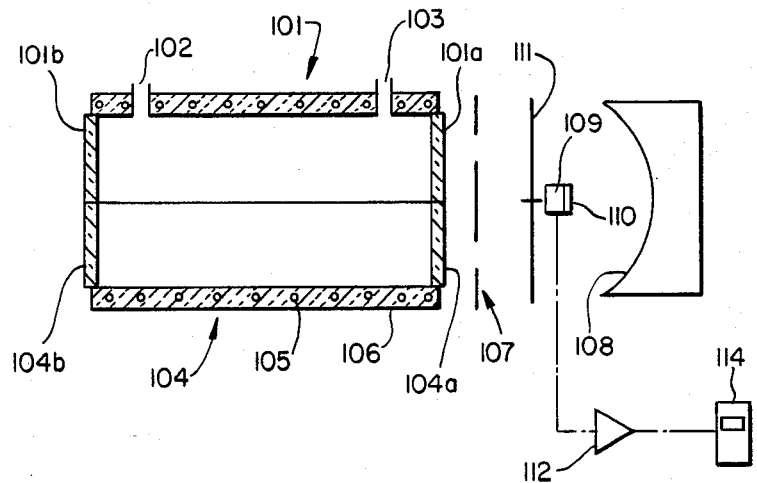

FIG. 7 shows still another embodiment of the present invention.

Referring now to FIG. 7, a sample cell 101 is provided with a sample gas-inlet 102 and a sample gas-outlet 103. A reference cell 104 is provided adjacent cell 101 in which a reference gas, which is a gas of the same composition as the sample gas but from which the ingredient the concentration of which is to be determined has been removed, is enclosed. The internal surfaces of both said cells 101 and 104 are equally mirror-finished, and said cells 101 and 104 are provided with respective cell-windows 101a and 101b and 104a and 104b at opposite ends thereof, respectively, said cell-window 101a, 101b, 104a and 104b being made of infrared ray transmitting material.

In addition, the cell length of the two cells 101 and 104, namely the optical length thereof from the outside surface of one cell-window 101a or 104a to the outside surface of the other cell-window 101b or 104b, is the same.

A heater 105 is wound around both cells 101 and 104 for heating gas enclosed in said cells to temperatures higher than 100° C. to radiate infrared rays so that the background infrared radiation will have only a negligible effect on the accuracy of measurement, and said heater is surrounded with insulating material 106.

A slit plate 107 is positioned just outside said cell-windows 101a and 104a, an equal size slit being provided for each cell so that the infrared rays passed from said sample cell 101 are equal to the infrared rays passed from said reference cell 104.

A generally parabolic reflecting mirror is positioned on the other side of the slit plate 107 from the cells 101 and 104 and an infrared detector 109 is positioned at the focal point for receiving infrared rays which are radiated from said sample gas and said reference gas and then reflected by said mirror 108. A filter 110 is provided between the mirror 108 and the detector 109 for transmitting only infrared rays having the specified wave lengths radiated from the ingredient the concentration of which is to be determined and interfering infrared rays radiated from said cells 101 and 104 and having the same wave length as said specified wave length of infrared rays radiated from the ingredient the concentration of which is to be determined. A chopper 111 is provided between the slit plate 107 and the mirror for causing infrared rays from said sample gas and infrared rays from said reference gas to fall alternately on said infrared detector 109, and said infrared detector 109 generating a pulsed electric signal corresponding to the infrared rays in the specified wave length delivered thereto during the revolution of said chopper 111.

An amplifier 112 is connected to detector 109 for amplifying electric signal from said detector 109, said amplifier 112 being connected a concentration-indicating mechanism 114 for indicating the concentrations of the ingredient the concentration of which is to be determined.

In the above described construction, infrared rays are radiated from said sample cell 101 and said reference cell 104 when said sample cell 101 and said reference cell 104 are heated to the appointed temperature by means of said heater 105. Infrared rays radiated from the ingredient the concentration of which is to be determined and having the specified wave length, for example a 4.3 μm band when determining the concentration of $CO_2$, background infrared rays from the walls, windows and the like of said sample cell 101 and background infrared rays from the walls, windows and the like of said reference cell 104 are received by said infrared detector 109 alternately through said filter 110 and the concentration of the ingredient is indicated by said indicating mechanism 114 according to the difference between the infrared rays radiated from the sample cell 101 and the infrared rays radiated from the reference cell 104. The concentration of the ingredient can thus be accurately detected by eliminating the influence of background infrared rays. It goes without saying that the concentration of the ingredient can be accurately detected on the basis of the difference between the absolute values of the infrared radiation even though the infrared radiation changes owing to the fouling of said cells 101 and 104 and said cell-windows 101a and 104a, changes in temperature, and the like.

Furthermore, it is not necessary to hold the desired temperature constant once the sample gas and the reference gas are heated to said desired temperature. For example the sample gas and the reference gas can be heated to the suitable temperature range and simultaneously temperature compensation can be carried out by means of a thermometer for measuring the temperature of the gas, or gas which was previously heated to high temperatures, can be put in said cell 101.

Infrared detectors and filters of various known constructions can be used for said infrared detector 109 and said filter 110. The concentration of different ingredients can be detected by exchanging said filter 110 for filters which transmit infrared rays of different wave lengths.

Figure 8:
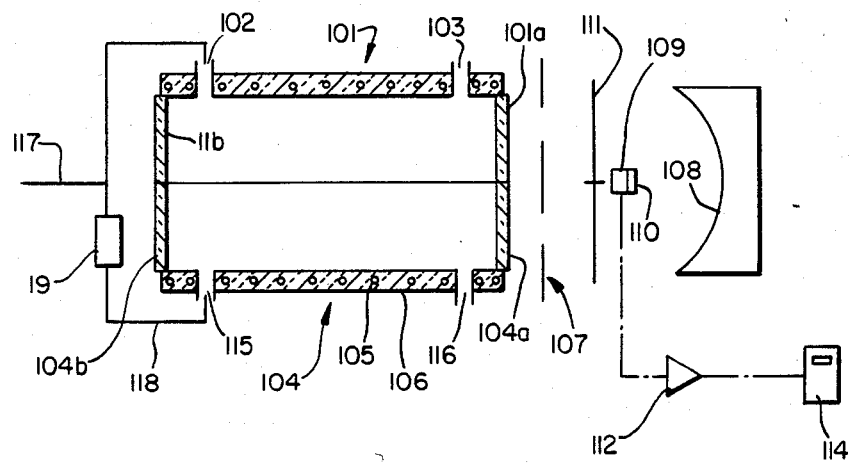

FIG. 8 shows another embodiment of the present invention. This embodiment differs from that of FIG. 7 in that reference cell 104 is provided with an inlet 115 and an outlet 116, said inlet 115 being connected by a branch pipe 118 to a sample gas feed pipe 117. An ingredient remover 119 is provided in branch pipe 118 for removing the ingredient the concentration of which is to be determined from the gas fed into said reference cell 104 to serve as the reference gas. Thus the interference due to presence of other ingredients in the sample gas can be eliminated, since the ingredients are contained in said sample cell 101 and said reference cell 104 in equal amounts.

Any gas can be used as the reference gas if it does not contain the ingredient the concentration of which is to be determined.

As described above, in the embodiments of FIG. 7 and FIG. 8, background infrared rays and interfering infrared rays, which are a main cause of errors in measurement, can be compensated for by providing a separate reference cell.

The infrared rays from the reference cell are subtracted from the infrared rays from the sample cell to detect the real value, or a value near thereto, of the infrared rays radiated from the ingredient the concentration of which is to be determined, whereby the concentration of the ingredient contained in the sample gas can be accurately detected by a simple apparatus.

We claim:

1. An infrared radiation gas analyzer for determining the concentration of an ingredient in a sample gas, comprising:

a sample gas containing means for containing a sample gas at a temperature at which the ingredient the concentration of which is to be determined will emit infrared radiation in a range characteristic of the ingredient and means for allowing said infrared radiation to escape from said containing means;

an optical chopper outside said containing means for interrupting the radiation escaping from said containing means;

a filter in the path of the radiation escaping from said containing means, said filter transmitting only radiation in said range;

an infrared radiation detector positioned for receiving the radiation passed by said filter and emitting a signal representative of the radiation received by the detector and which is representative of the concentration of the ingredient the concentration of which is to be determined in the sample gas.

2. An infrared radiation gas analyzer as claimed in claim 1 in which said sample gas containing means is a sample gas container having heating means for heating a sample gas in said container.

3. An infrared radiation gas analyzer as claimed in claim 1 further comprising a condensing lens between said chopper and said filter for focusing the radiation on said filter.

4. An infrared radiation gas analyzer as claimed in claim 1 in which said containing means is unheated, and further comprising sample gas feed means connected to said containing means for heating the sample gas and supplying it to said containing means.

5. An infrared radiation gas analyzer as claimed in claim 1 in which said containing means is an elongated container, and said means for allowing said infrared radiation to escape from said containing means comprises a window in one end of said container.

6. An infrared radiation gas analyzer as claimed in claim 1 in which said containing means is an elongated container having a sample gas inlet at one end and a sample gas outlet at the other end, and further comprising heater means around said one end of said container for heating the sample gas, and said means for allowing said infrared radiation to escape from said containing means is a window in the other end of said container opening laterally of said container adjacent said gas outlet.

7. An infrared radiation gas analyzer as claimed in claim 1 further comprising a reference gas containing means adjacent said sample gas containing means for containing a gas having the same composition as said sample gas but without the ingredient the concentration of which is to be determined, said reference gas containing means having means for allowing infrared radiation to escape therefrom, said chopper being adjacent said lastmentioned means for interrupting the radiation escaping from said means in both containing means, a slit plate between said containing means and said chopper having a slit opposite each of the respective means for allowing infrared radiation to escape, a parabolic mirror on the opposite side of said chopper from said containing means for receiving radiation therefrom, said filter and radiation detector being at the focal point of said mirror and receiving pulses of radiation from said mirror and emitting a pulsed signal, and means connected to said radiation detector for subtracting the pulses of the pulsed signal from each other to obtain an output representative of the concentration of the ingredient.

8. An infrared radiation gas analyzer as claimed in claim 7 further comprising sample gas feed means connected to said sample gas containing means for feeding the sample gas thereto, branch conduit means connected between said sample gas feed means and said reference gas containing means, and an ingredient remover means in said branch conduit for removing from the sample gas the ingredient the concentration of which is to be determined.

* * * * *